United States Patent [19]

Makita et al.

[11] Patent Number: 4,647,636

[45] Date of Patent: Mar. 3, 1987

[54] PROCESS FOR PREPARING HIGHLY WATER-ABSORBENT RESIN

[75] Inventors: Muneharu Makita, Takatsuki; Jun-ichi Maeno, Osaka, both of Japan

[73] Assignee: Arakawa Kagaku Kogyo Kabushiki Kaisha, Osaka, Japan

[21] Appl. No.: 774,846

[22] Filed: Sep. 11, 1985

[30] Foreign Application Priority Data

Sep. 19, 1984 [JP] Japan ................................. 59-196068

[51] Int. Cl.$^4$ ............................................. C08F 2/32
[52] U.S. Cl. .................................... 526/206; 526/210; 526/306; 526/317.1
[58] Field of Search ........................ 526/206, 207, 210

[56] References Cited

U.S. PATENT DOCUMENTS 3,948,866  4/1976  Pennewiss ............................ 526/287
4,500,649  2/1985  Tanaka ................................. 526/207

*Primary Examiner*—Christopher Henderson
*Attorney, Agent, or Firm*—Armstrong, Nikaido, Marmelstein & Kubovcik

[57] ABSTRACT

A process for preparing a highly water-absorbent resin by a reversed-phase suspension polymerization method using an aqueous solution of a monomer containing an alkali metal salt of acrylic or methacrylic acid, water-soluble polymerization initiator, protective colloid, hydrophobic organic solvent and if required, dispersing agent, the process being characterized in that the protective colloid is a copolymer comprising:

(A) about 50 to about 97 mole % of styrene and/or alkyl-substituted derivative thereof, (B) 0 to about 50 mole % of dialkylaminoalkyl acrylate or methacrylate and/or dialkylaminoalkyl acrylamide or methacrylamide, (C) about 3 to about 15 mole % of glycidyl acrylate and/or glycidyl methacrylate and (D) 0 to about 30 mole % of an unsaturated monomer which can be copolymerized with the component A, B or C.

15 Claims, No Drawings

PROCESS FOR PREPARING HIGHLY WATER-ABSORBENT RESIN

FIELD OF THE INVENTION

This invention relates to a process for preparing water-absorbent resins and more particularly to a process for preparing water-absorbent resins outstanding in water-absorbency, water-absorbing rate, gel strength and the like and usable with safety by a reversed-phase suspension polymerization method using an aqueous solution of a monomer containing an alkali metal salt of acrylic or methacrylic acid.

BACKGROUND OF THE INVENTION

Water-absorbent resins are used for manufacture of sanitary articles such as sanitary napkins, diapers and disposable dusters, and other materials, e.g. water-holding materials used in agriculture or horticulture, materials for coagulating sludge, those for preventing dew condensation in buildings and those for removing water from oils.

Known water-absorbent resins include cross-linked carboxymethyl cellulose, partially cross-linked polyoxyethylene, hydrolyzed starch-acrylonitrile graftcopolymer, partially cross-linked polyacrylate, vinyl alcohol-acrylate copolymer, etc. The properties of conventional water-absorbent resins are greatly affected by the producing process, and there is no water-absorbent resin known in the art which possesses all the required properties including water-absorption power, water-absorbing rate, gel strength and safety. For example, conventional water-absorbent resins have the drawbacks of being low in water-absorbency, or low in gel strength after absorption of water although high in water-absorbency, leaving the gel soggy after absorption of water, namely failing to give a dry feeling, and remaining as partially dried lumps of particles after absorption of water.

It is known to improve the gel strength of water-absorbent resin after absorption of water by increasing the cross linking density of the resin. However, this method has the serious defect of reducing the water-absorbency critically required of water-absorbent resins. Further although the problem of remaining as partially dried lumps of particles can be resolved by improving the properties of particulate surface for example with a cross linking agent such as ethylene glycol diglycidyl ether, the cross linking agent is likely to irritate the human skin and thus poses a hazard problem from hygienic viewpoints when remaining in the resin.

Preferred examples of known water-absorbent resins include bead polymers prepared by polymerizing an acrylate by a reversed-phase suspension polymerization method using cellulose ester or cellulose ether as a protective colloid (Japanese Unexamined Patent Publication No. 158209/1982) or using sorbitan fatty acid ester as a dispersing agent and hydroxyethyl cellulose as a protective colloid (Japanese Unexamined Patent Publication No. 76419/1981).

However, the polymers prepared by these methods fail to satisfactorily meet the property requirements for water-absorbent resins. Particularly the gel strength of the polymers remains to be further improved. The disclosed methods give polymers which tend to readily cause blocking by standing at room temperature because of the high hydrophilic property of protective colloid used. With this shortcoming, the methods additionally require a cumbersome procedure of washing with heating the protective colloid with a solvent after the reversed-phase suspension polymerization to remove the colloid from the bead polymer prepared, hence also disadvantageous in terms of procedures.

SUMMARY OF THE INVENTION

It is an object of this invention to provide a novel water-absorbent resin having all the properties required of water-absorbent resins such as a high water-absorbency, water-absorbing rate, gel strength and safety and a process for preparing the same.

It is another object of the invention to provide a water-absorbent resin having a high water-absorbency and a great gel strength and a process for preparing the same.

It is a further object of the invention to provide a process for preparing a water-absorbent resin outstanding in the foregoing properties which process is free from the drawbacks of conventional processes.

These objects and other features of the present invention will become apparent from the following description.

This invention provides a process for preparing a highly water-absorbent resin by a reversed-phase suspension polymerization method using an aqueous solution of a monomer containing an alkali metal salt of acrylic or methacrylic acid, water-soluble polymerization initiator, protective colloid, hydrophobic organic solvent and if required, dispersing agent, the process being characterized in that the protective colloid is a copolymer comprising:

(A) about 50 to about 97 mole % of styrene and/or alkyl-substituted derivative thereof (hereinafter referred to as "component A"), (B) 0 to about 50 mole % of dialkylaminoalkyl acrylate or methacrylate and/or dialkylaminoalkyl acrylamide or methacrylamide (hereinafter referred to as "component B"), (C) about 3 to about 15 mole % of glycidyl acrylate and/or glycidyl methacrylate (hereinafter referred to as "component C") and (D) 0 to about 30 mole % of an unsaturated monomer which can be copolymerized with the component A, B or C (hereinafter referred to as "component D").

This invention also provides a highly water-absorbent resin prepared by the foregoing process.

We conducted extensive research and found that when using the above-specified protective colloid and if required, a dispersing agent in the conventional reversed-phase suspension polymerization method, there is prepared a water-absorbent resin free from the drawbacks of conventional processes and having excellent properties which comply with the foregoing objects of the invention. This invention has been accomplished based on this novel finding.

DETAILED DESCRIPTION OF THE INVENTION

It is critical in this invention to use as the protective colloid the copolymer (cationic copolymer) comprising the components A, B (when present), C and D (when present) in the above-specified proportions.

Examples of the alkyl-substituted derivative of styrene of the component A constituting the cationic copolymer are derivatives thereof substituted with lower alkyl having 1 to 6 carbon atoms on the aromatic ring such as vinyltoluene and those substituted with lower alkyl having 1 to 6 carbon atoms on the vinyl group such as α-methylstyrene, etc.

Examples of the dialkylaminoalkyl acrylate or methacrylate, i.e. one constituent of the component B are di($C_{1-6}$alkyl)amino($C_{1-6}$-alkyl) acrylates or methacrylates such as dimethylaminomethyl acrylate, dimethylaminoethyl acrylate, dimethylaminopropyl acrylate, diethylaminomethyl acrylate, diethylaminoethyl acrylate, diethylaminopropyl acrylate, dimethylaminomethyl methacrylate, dimethylaminoethyl methacrylate, dimethylaminopropyl methacrylate, diethylaminomethyl methacrylate, diethylaminoethyl methacrylate, diethylaminopropyl methacrylate, etc. Examples of the dialkylaminoalkyl acrylamide or methacrylamide, i.e. the other constituent of the component B are di($C_{1-6}$alkyl)amino($C_{1-6}$alkyl) acrylamides or methacrylamides such as dimethylaminomethyl acrylamide, dimethylaminoethyl acrylamide, dimethylaminopropyl acrylamide, diethylaminomethyl acrylamide, diethylaminoethyl acrylamide, diethylaminopropyl acrylamide, dimethylaminomethyl methacrylamide, dimethylaminoethyl methacrylamide, dimethylaminopropyl methacrylamide, diethylaminomethyl methacrylamide, diethylaminoethyl methacrylamide, diethylaminopropyl methacrylamide, etc. These compounds can be used singly or at least two of them are usable in admixture.

The component C is an unsaturated monomer containing an epoxy group and thus is readily available as the material for the water-absorbent resins of this invention.

The component D is an unsaturated monomer which can be copolymerized with the component A, B or C and which is selected from the monomers unreactive with the dialkylamino group of the component B and with the epoxy group of the component C. Examples of the monomers are alkyl acrylates such as methyl acrylate, ethyl acrylate, butyl acrylate and 2-ethylhexyl acrylate; alkyl methacrylates such as methyl methacrylate, ethyl methacrylate, butyl methacrylate and 2-ethylhexyl methacrylate; and other compounds such as acrylonitrile, acrylamide, methacrylamide, vinyl acetate, etc.

The amount of the component A affects the solubility in the organic solvent used in reversed-phase suspension polymerization, the function of the protective colloid in the polymerization, the tendency of the water-absorbent resin to cause blocking, etc. and is in the range of about 50 to about 97% (mole % herein and hereinafter), preferably about 70 to about 95%. The presence of less than about 50% of the component A results in a water-absorbent resin which tends to induce blocking and leads to a major proportion of fine grain polymer (less than about 0.01 mm in particle size) with the result that the polymer obtained is difficult to handle, hence undesirable. The content of more than about 97% diminishes the amounts of other components, particularly component B, consequently impairing the function of the protective colloid and lowering the gel strength of the polymer obtained, hence undesirable.

The amount of the component B is 0 to about 50%, preferably about 3 to about 30%. The component B used is related to the function of the protective colloid and also affects the particle size of the polymer obtained and the gel strength. The use of the component B in the above-specified range serves to enhance the function of the protective colloid and to give stable bead polymers. With more than about 50% of the component B, the polymer prepared has a reduced particle size, and is more likely to cause blocking and to impart a dry feeling in a lesser degree after absorption of water.

The component C is used in an amount of about 3 to about 15%. The component C acts in synergy with the component B to give an improved function of the protective colloid and a higher water-absorbency, greater water-absorbing rate, outstanding gel strength, enhanced dry feeling and other improved properties to the resin. The use of less than about 3% of the component C tends to decrease the water-absorbing rate, whereas the presence of more than about 15% deteriorates the function of the protective colloid, making it difficult to obtain a stable bead polymer.

The use of the component D is not critical in this invention. The amount of the component D used should be in a range which will not impair the characteristics attributable to the use of the components A to C. Generally the maximum amount is about 30%. The presence of over about 30% reduces the solubility of the protective colloid in the organic solvent to be used in the reversed-phase suspension polymerization and impairs the function of the protective colloid, hence undesirable.

The cationic polymer used as the protective colloid and comprising the components A to D according to this invention can be easily prepared by conventional methods such as solution polymerization method and suspension polymerization method. Polymerization initiators commonly used in the art such as azobisisobutyronitrile and like oil-soluble azo-type polymerization initiators can be employed in these methods.

It is preferred to prepare the cationic polymer by the suspension polymerization method. The suspension polymerization method is carried out for example by incorporating polyvinyl alcohol or gelatin in deionized water, heating the mixture to a suitable temperature in a nitrogen atmosphere, adding dropwise the components A to D and a polymerization initiator in specified proportions, maintaining the resulting mixture at the temperature until completion of the polymerization, filtering the reaction product and drying the solids under a reduced pressure to afford the desired bead cationic polymer. The polymer can be prepared also by the solution polymerization method. The solution polymerization method can be performed for example by heating a suitable hydrophobic organic solvent such as n-pentane, n-hexane and cyclohexane and adding dropwise specific amounts of the components A to D and a polymerization initiator to the solvent to induce polymerization or by dissolving or dispersing the components A to D and the polymerization initiator in the solvent and heating the solution or dispersion to a suitable temperature for polymerization or by the combination of these steps. The amount of the polymerization initiator used in any of the polymerization methods is in the range of about 0.001 to about 5.0% by weight, preferably about 0.01 to about 1.0% by weight, based on the total weight of the monomers (components A to D) used.

The use of the cationic polymer thus obtained as the protective colloid is important in the present invention because its use enables the production of a water-absorbent resin having the desired good characteristics. The protective colloid can be used in a ratio by weight of the colloid to a monomer containing an alkali metal salt of acrylic acid or methacrylic acid of 0.5:99.5 to 30:70, preferably 0.7:99.3 to 10:90.

When required, a dispersing agent can be used in the process of this invention. Examples of useful dispersing agents include sorbitan fatty acid esters and saccharose fatty acid esters. The dispersing agent used results in a more uniform distribution of particle size in the bead polymer obtained than when using the protective colloid alone. The compounds exemplified above as the dispersing agent are those capable of completely meeting the food additive requirements under official regulations as seen from their conventional use as food emulsifiers and thus are safely usable, hence suitable also in this respect for preparation of water-absorbent resins. Saccharose fatty acid esters are preferred because their use is effective in giving the desired degree of water-absorbing rate and gel strength to water-absorbent resins.

Preferred sorbitan fatty acid esters are those having a hydrophilic-lipophilic balance (HLB) of about 2 to about 12. Those less than about 2 in HLB tend to reduce the dispersibility, whereas those more than about 12 in HLB are prone to produce polymers in the form of not bead but fine grain emulsion. Saccharose fatty acid esters useful in this invention are not particularly limited as to HLB and any of those commercially available with HLB of about 1 to about 15 can be used with good results.

The amount of the dispersing agent is suitably determined and is preferably in the range of about 0.001 to about 10% by weight based on the monomer containing an alkali metal salt of acrylic acid or methacrylic acid to be subjected to polymerization reaction. Below about 0.001% by weight, the desired effect can not be achieved, whereas over about 10% by weight, an improved effect is not produced and economical disadvantages will result.

A monomer is polymerized in the presence of the protective colloid with or without the dispersing agent according to this invention. The monomer to be used in this invention is one containing an alkali metal salt of acrylic acid or methacrylic acid, considering the water-absorbency, safety and rot-resistance of the water-absorbent resin obtained, etc. The monomer of the invention may comprise an alkali metal salt of acrylic acid or methacrylic acid alone or in mixture with such salt or may be a combination of such salt as the main component and another monomer Examples of other monomers to be conjointly used can be any of those heretofore used in preparing water-absorbent resins of the acrylate or methacrylate type such as methyl acrylate, ethyl acrylate, butyl acrylate, 2-ethylhexyl acrylate, methyl methacrylate, ethyl methyacrylate, butyl methacrylate, 2-ethylhexyl methacrylate, acrylonitrile, acrylamide, methacrylamide, vinyl acetate, etc. The preferred amount of the other monomer to be conjointly used is up to about 20% by weight based on the alakli metal salt of acrylic acid or methacrylic acid. The neutralization degree of acrylic or methacrylic acid to be achieved by the alkali metal is suitably determined depending on the safety and water-absorbency of the polymer obtained and the like. Preferred neutralization degree is in the range of about 50% to about 95%. If the neutralization degree is far lower than about 50%, the polymerization takes place in a lower degree and gives polymers with a decreased water-absorbency. The neutralization degree of over about 95% provides no further advantage.

The monomer in the form of an aqueous solution is subjected to the reversed-phase suspension polymerization reaction of this invention. The concentration of the total monomers in the aqueous solution affects the polymerization stability and molecular weight of the polymer obtained (degree of cross linking) and is adjusted to about 35 to about 80% by weight, preferably about 40 to about 70% by weight. The concentration of less than about 35% by weight diminishes the stability of suspension polymerization and is apt to produce agglomerates as a by-product. It is difficult to increase the concentration of the monomer to over about 80% by weight because of the saturation concentration of the monomer.

The water-soluble polymerization initiator to be used in the reversed-phase suspension polymerization in the presence of the aqueous solution of the monomer as the protective colloid with or without the dispersing agent can be any of polymerization initiators commonly used in the art and including water-soluble persulfates such as ammonium persulfate and potassium persulfate, and water-soluble azo-type initiators such as azobis-(2-amidinopropane)hydrochloride, etc. The amount of the polymerization initiator is generally about 0.001 to about 5.0% by weight, preferably about 0.01 to about 1.0% by weight, based on the total weight of the monomers.

When the monomer is polymerized with the water-soluble persulfate, cross-linking proceeds without using a cross-linking agent. However, when the water-soluble azo-type polymerization initiator is used, cross-linking may occur with difficulty or is unlikely to take place. In the latter case, a cross-linking agent should be added to the aqueous solution of monomers containing an alkali metal salt of acrylic acid or methacrylic acid. Useful cross-linking agents can be any of those known in the art such as methylenebisacrylamide, methylenebismethacrylamide and the like bisacrylamides, divinyl compounds to be described below, etc.

(i) Diacrylates (dimethacrylates) represented by the formula $$CH_2=CH \quad HC=CH_2 \atop | \quad\quad\quad\quad | \atop O=C-O-X-O-C=O \quad (1)$$

wherein X represents ethylene, propylene, 2-hydroxypropylene, a group 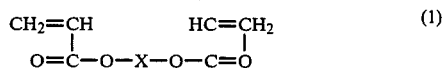 or a group

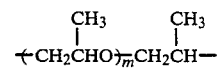

and n and m are an integer of 5 to 40.

The compounds of the formula (1) can be prepared by reacting polyol such as ethylene glycol, propylene glycol, glycerin, polyethylene glycol, polypropylene glycol and the like with acrylic acid or methacrylic acid.

(ii) Diacrylamides represented by the formula $$CH_2=CH \quad HC=CH_2 \atop | \quad\quad\quad\quad\quad | \atop O=CNH\text{\small+}CH_2CH_2NH\text{\small)}_{\overline{l}}C=O \quad (2)$$

wherein l is 2 or 3.

The compounds of the formula (2) can be prepared by reacting polyalkylenepolyamine such as diethylenetriamine, triethylenetetramine and the like with acrylic acid.

Of these compounds, preferable are bisacrylamides such as N,N-methylenebisacrylamide, N,N-methylenebismethacrylamide and the like.

The cross-linking agent used is effective in increasing the gel strength of the polymer obtained. The amount of the cross-linking agent is about 0.001 to about 0.3% by weight, preferably about 0.005 to about 0.1% by weight, based on the alkali metal salt of acrylic or methacrylic acid which is the main component of the monomer.

The hydrophobic organic solvent used as the dispersing medium in this invention affects the stability of the polymer prepared by the reversed-phase suspension polymerization method and is generally selected from solvents of aliphatic or alicyclic hydrocarbon type such as n-pentane, n-hexane, n-heptane, cyclohexane, ligroin, etc. among which cyclohexane, n-pentane and n-hexane are preferred.

The reversed-phase suspension polymerization method of this invention can be carried out in the same manner as in conventional methods with the exception of using the foregoing specific protective colloid with or without the dispersing agent. For example, the following method can be employed. Into a suitable reactor are placed the hydrophobic organic solvent, protective colloid and when required, the dispersing agent to obtain a solution or dispersion. Thereto is added in a nitrogen atmosphere an aqueuos solution of a mixture of water-soluble polymerization initiator and monomer containing an alkali metal salt of acrylic or methacrylic acid in specific proportions. The system is heated to a temperature of about 40° to about 80° C. and maintained at the same temperature for a specific period of time. The water is removed by azeotropic distillation. The residue is filtered and the solids are dried under reduced pressure. In this way, a desired bead polymer can be prepared which has a mean particle size in the range of about 0.01 to about 2 mm (about 0.01 to about 0.2 mm when using the dispersing agent).

According to the foregoing method, polymerization reaction can stably proceed due to the use of specific protective colloid with or without the dispersing agent, consequently affording a bead polyer adequate in particle size and uniform in distribution of particle size. The polymer thus obtained has the advantages of being outstanding in water-absorbency, water-absorbing rate, gel strength and other properties and free from the adhesion between particles (partially dried lumps of particles) and from the stickiness of gel after absorption of water.

It remains to be clarified why the polymers with such excellent characteristics can be prepared. It is presumably because an ionic bond is produced between the protective colloid and the the alkali metal salt of acrylic or methacrylic acid constituting the core of polymer particle due to the former being a cationic copolymer so that a coacervation structure is formed, giving a stable bead polymer and so that the cationic copolymer present as the protective colloid is localized in the surface of polymer particle by the cross linking resulting from the ionic bond, thereby improving the properties of the surface. Another possible cause may be that since the cationic copolymer used in this invention has epoxy group which is a functional group reactive with carboxyl or carboxylate group, there occurs an addition reaction between the protective colloid and the alkali metal salt of acrylic or methacrylic acid in the reversed-phase suspension polymerization, thereby selectively improving the properties of surface of bead polymer thus obtained so that the polymer surface assumes a cross linking structure. Because the tertiary amine contained as the component B in the cationic copolymer acts as a catalyst in the foregoing addition reaction, the addition reaction smoothly proceeds, leaving no unreacted epoxy group and thus involving no hazard problem of irritating the human skin. Whatever the cause may be, the bead polymers prepared according to this invention are excellent in water-absorbency, water-absorbing rate, gel strength and the like. Further the process of this invention gives bead polymers with a particle surface having a cross linking structure formed due to the use of the specific cationic copolymer as the protective colloid in the reversed-phase suspension polymerization. Accordingly this invention eliminates the need to perform after-cross-linking a subsequent cross-linking step using a cross-linking agent such as ethylene glycol diglycidyl ether critically used in the prior art to increase the gel strength and water-absorbing rate, hence is free from the hygienic problem of irritating the human skin which is attributable to the use of the cross-linking agent. For this reason, the polymers thus obtained are very useful as water-absorbent resins, particulary as sanitary articles.

The water-absorbent resins produced by the process of this invention are usable in various areas in which the same type of water-absorbent resins have been employed. Further they can be used with the good results due to the aforesaid characteristics.

This invention is described below in more detail with reference to the following reference examples for preparation of protective colloids to be used in this invention and examples for the process of this invention to which the invention, however, is in no way limited.

REFERENCE EXAMPLE 1

Deionized water (450 g) was placed into a 1-liter flask equipped with a stirrer, reflux condenser, thermometer and inlet tube for nitrogen. A 0.6 g quantity of gelatin serving as a dispersing agent was dissolved in the deionized water. The system was heated to 80° C. in a nitrogen atmosphere. In the system was dispersed a solution of 1.5 g of azobisisobutyronitrile in 126.7 g (90 mole %) of styrene, 17.6 g (7 mole %) of diethylaminoethyl methacrylate and 5.7 g (3 mole %) of glycidyl methacrylate. The dispersion was maintained at 80° C. for 3 hours in a nitrogen atmosphere with stirring to complete the reaction. The system was cooled to 40° C. or lower and filtered. The solids were dried under a reduced presure, giving a bead polymer having a particle size of 0.1 and 2 mm which is hereinafter referred to as "protective colloid A".

REFERENCE EXAMPLE 2

The same procedure as in Reference Example 1 was repeated with the exception of using 127.6 g (90 mole %) of styrene, 12.6 g (5 mole %) of diethylaminoethyl methacrylate and 9.8 g (5 mole %) of glycidyl methacrylate, thereby affording a bead polymer having a particle size of 0.1 to 2 mm which is hereinafter called "protective colloid B".

REFERENCE EXAMPLE 3

The same procedure as in Reference Example 1 was repeated with the exception of using 102.4 g (78 mole %) of styrene, 35.0 g (15 mole %) of diethylaminoethyl methacrylate and 12.6 g (7 mole %) of glycidyl methacrylate, thereby affording a bead polymer having a particle size of 0.1 to 2 mm which is hereinafter called "protective colloid C".

REFERENCE EXAMPLE 4

The same procedure as in Reference Example 1 was repeated with the exception of using 118.5 g (85 mole %) of styrene, 12.45 g (5 mole %) of diethylaminoethyl methacrylate and 19.05 g (10 mole %) of glycidyl methacrylate, thereby affording a bead polymer having a particle size of 0.1 to 2 mm which is hereinafter called "protective colloid D".

REFERENCE EXAMPLE 5

The same procedure as in Reference Example 1 was repeated with the exception of using 139.9 g (95 mole %) of styrene and 10.1 g (5 mole %) of glycidyl methacrylate, thereby affording a bead polymer having a particle size of 0.1 to 2 mm which is hereinafter called "protective colloid E".

REFERENCE EXAMPLE 6

The same procedure as in Reference Example 1 was repeated with the exception of using 130.2 g (90 mole %) of styrene and 19.8 g (10 mole %) of glycidyl methacrylate, thereby affording a bead polymer having a particle size of 0.1 to 2 mm which is hereinafter called "protective colloid F".

REFERENCE EXAMPLE 7

The same procedure as in Reference Example 1 was repeated with the exception of using 113.9 g (80 mole %) of styrene, 12.7 g (5 mole %) of diethylaminoethyl methacrylate, 9.7 g (10 mole %) of glycidyl methacrylate and 13.7 g (5 mole %) of methyl methacrylate, thereby affording a bead polymer having a particle size of 0.1 to 2 mm which is hereinafter called "protective colloid G".

REFERENCE EXAMPLE 8

Xylene (180 g) was placed into a 1-liter flask equipped with a stirrer, reflux condenser, thermometer and inlet tube for nitrogen. The system was heated to 80° C. in a nitrogen atmosphere. A 1.05 g quantity of azobisisobutyronitrile was dissolved in 357.4 g (90 mole %) of styrene, 35.3 g (5 mole %) of diethylaminoethyl methacrylate and 27.3 g (5 mole %) of glycidyl methacrylate. A half portion of the solution was charged in the flask and stirred at 80° C. in a nitrogen atmosphere for 1 hour. The other half was added dropwise to the flask over a period of 30 minutes. The mixture was maintained at the same temperature for 8 hours with stirring to complete the reaction. The system was heated and the xylene was distilled off under a reduced pressure of about 20 mmHg, giving a resinous product (hereinafter referred to as "protective colloid H").

EXAMPLE 1

A 240 g quantity of cyclohexane was placed into a 1-liter flask equipped with a stirrer, reflux condenser, thermometer and inlet tube for nitrogen. A 3.0 g portion of the protective colloid A was dispersed in the cyclohexane.

Acrylic acid (75.8 g) was neutralized with 164.2 g of a 27% aqueous solution of potassium hydroxide (72 mole % based on the acrylic acid) with ice cooling. In the solution were dissolved 0.016 g of N,N-methylenebisacrylamide and 0.12 g of 2,2-azobis-(2-amidinopropane)dihydrochloride (product of WAKO JUNYAKU KABUSHIKI KAISHA, Japan, available under the trademark "V-50").

The solution thus obtained was placed into the flask to give a dispersion. The dispersion was stirred in a nitrogen atomosphere at 60° C. for 1 hour to complete the reaction. The reaction mixture was subjected to azeotropic distillation to remove the water and cyclohexane. The residue was cooled to 40° C. or lower and filtered. The solids were dried under a reduced pressure, giving a bead polymer having a particle size of 0.01 to 2 mm (hereinafter called "water-absorbent resin A").

EXAMPLE 2

A bead polymer having a particle size of 0.01 to 2 mm (hereinafter called "water-absorbent resin B") was prepared in the same manner as in Example 1 with the exception of using the protective colloid B in place of the protective colloid A used in Example 1.

EXAMPLE 3

A bead polymer having a particle size of 0.01 to 2 mm (hereinafter called "water-absorbent resin C") was prepared in the same manner as in Example 1 with the exception of using the protective colloid B in a reduced amount of 0.84 g in place of the protective colloid A used in Example 1.

EXAMPLE 4

A bead polymer having a particle size of 0.01 to 2 mm (hereinafter called "water-absorbent resin D") was prepared in the same manner as in Example 1 with the exception of using the protective colloid B in an increased amount of 12.0 g in place of the protective colloid A used in Example 1.

EXAMPLE 5

A bead polymer having a particle size of 0.01 to 2 mm (hereinafter called "water-absorbent resin E") was prepared in the same manner as in Example 1 with the exception of using the protective colloid C in place of the protective colloid A used in Example 1.

EXAMPLE 6

A bead polymer having a particle size of 0.01 to 2 mm (hereinafter called "water-absorbent resin F") was prepared in the same manner as in Example 1 with the exception of using the protective colloid D in place of the protective colloid A used in Example 1.

EXAMPLE 7

A bead polymer having a particle size of 0.01 to 2 mm (hereinafter called "water-absorbent resin G") was prepared in the same manner as in Example 1 with the exception of using the protective colloid E in place of the protective colloid A used in Example 1.

EXAMPLE 8

A bead polymer having a particle size of 0.01 to 2 mm (hereinafter called "water-absorbent resin H") was prepared in the same manner as in Example 1 with the exception of using the protective colloid F in place of the protective colloid A used in Example 1.

EXAMPLE 9

A bead polymer having a particle size of 0.01 to 2 mm (hereinafter called "water-absorbent resin I") was prepared in the same manner as in Example 1 with the exception of using the protective colloid G in place of the protective colloid A used in Example 1.

EXAMPLE 10

A bead polymer having a particle size of 0.01 to 2 mm (hereinafter called "water-absorbent resin J") was prepared in the same manner as in Example 1 with the exception of using the protective colloid B in place of the protective colloid A used in Example 1 and polyethylene glycol diacrylate (ethylene ether groups being 20 in number) as a cross-linking agent in place of N,N-methylenebisacrylamide used in Example 1.

EXAMPLE 11

A bead polymer having a particle size of 0.01 to 2 mm (hereinafter called "water-absorbent resin K") was prepared in the same manner as in Example 1 with the exception of using the protective colloid B in place of the protective colloid A used in Example 1 and diethylenetriamine diacrylamide as a cross-linking agent in place of N,N-methylenebisacrylamide used in Example 1.

EXAMPLE 12

A bead polymer having a particle size of 0.01 to 2 mm (hereinafter called "water-absorbent resin L") was prepared in the same manner as in Example 1 with the exception of using the protective colloid B in a reduced amount of 1.20 g in place of the protective colloid A used in Example 1 and 0.12 g of saccharose fatty acid ester (product of DAIICHI KOGYO SEIYAKU KABUSHIKI KAISHA, Japan, available under the trademark DK Ester F-20 (HLB 2)) as a dispersing agent.

EXAMPLE 13

A bead polymer having a particle size of 0.01 to 2 mm (hereinafter called "water-absorbent resin M") was prepared in the same manner as in Example 1 with the exception of using the protective colloid B in a reduced amount of 1.20 g in place of the protective colloid A used in Example 1 and 0.12 g of saccharose fatty acid ester (product of DAIICHI KOGYO SEIYAKU KABUSHIKI KAISHA, Japan, available under the trademark DK Ester F-50 (HLB 6)) as a dispersing agent.

EXAMPLE 14

A bead polymer having a particle size of 0.01 to 2 mm (hereinafter called "water-absorbent resin N") was prepared in the same manner as in Example 1 with the exception of using the protective colloid B in a reduced amount of 1.20 g in place of the protective colloid A used in Example 1 and 0.12 g of saccharose fatty acid ester (product of DAIICHI KOGYO SEIYAKU KABUSHIKI KAISHA, Japan, available under the trademark DK Ester F-140 (HLB 13)) as a dispersing agent.

EXAMPLE 15

A bead polymer having a particle size of 0.01 to 2 mm (hereinafter called "water-absorbent resin O") was prepared in the same manner as in Example 1 with the exception of using the protective colloid B in a reduced amount of 1.20 g in place of the protective colloid A used in Example 1 and 0.12 g of sorbitan monostearate (HLB 4.7) as a dispersing agent.

COMPARISON EXAMPLE 1

A bead polymer having a particle size of 0.01 to 2 mm (hereinafter called "water-absorbent resin a") was prepared in the same manner as in Example 1 with the exception of using ethyl cellulose in place of the protective colloid A used in Example 1.

The water-absorbent resins obtained above were tested to determine the water-absorbency, water-absorbing rate, gel strength and consistency of gel after absorption of water by the following methods.

1. Water-absorbency (a) A 150 g quantity of deionized water and 0.12 g of the water-absorbent resin sample were placed into a 200 ml beaker and the mixture was left to stand for 30 minutes. The mixture was passed through a 200-mesh gauze to separate the water. The weight of the water thus separated was measured. The water-absorbency of the sample was given by the following equation.

$$\text{Water-absorbency} = \frac{\left(\begin{array}{c}\text{Weight of water}\\ \text{initially present}\end{array}\right) - \left(\begin{array}{c}\text{Weight of water}\\ \text{separated}\end{array}\right)}{\text{Weight of water-absorbent resin sample}}$$

(b) The water-absorbency was determined by performing the same test as in (a) with the exception of using a 0.9% aqueous solution of sodium chloride in place of deionized water.

2. Water-absorbing rate

A 50 g quantity of a physiological saline solution (0.9% aqueous solution of sodium chloride) and a stirring rod were placed in a 100 ml beaker and the solution was stirred with a magnetic stirrer at a rate of 600 rpm. Into the beaker was charged 2.0 g of the water-absorbent resin sample to cause gellation by hygroscopic swelling. The gellation subdued the fluidity, precluding the agitation from inducing the swirl. The water-absorbing rate was expressed in terms of the time taken from the addition of water-absorbent resin sample until the cessation of swirl.

3. Gel strength

A physiological saline solution (60 g) and 2.0 g of the water-absorbent resin sample were mixed together to obtain a gel (hereinafter referred to as "30-fold gel"). The hardness (surface hardness) of the gel was measured by Neocurdmeter (trade name, product of IIO DENKI KABUSHIKI KAISHA, Japan). The surface hardness of the gel is expressed as the resistance of the gel to the force with which the pressure-sensitive axle is forced forward against the gel in the surface of the sample.

4. Consistency of gel

The stickiness of the gel was evaluated based on the consistency of the 30-fold gel obtained with use of Neocurdmeter. The consistency of the gel refers to the specific viscosity which is commensurate with the friction force of the gel against the flow thereof.

Table 1 below shows the results obtained by carrying out the foregoing test methods.

TABLE 1

| Water absorbent resin sample No. | Water-absorbency (g/g) | | Water-absorbing rate (sec) | Gel strength (dyne/cm$^2$) | Consistency (dyne sec/cm$^3$) |
| --- | --- | --- | --- | --- | --- |
| | Deionized water | 0.9% sol. of sodium chloride | | | |
| A (Ex. 1) | 720 | 65 | 20 | $1.2 \times 10^4$ | $2.0 \times 10^4$ |
| B (Ex. 2) | 720 | 65 | 15 | $5.2 \times 10^4$ | $5.0 \times 10^4$ |
| C (Ex. 3) | 720 | 65 | 15 | $4.3 \times 10^4$ | $6.7 \times 10^4$ |
| D (Ex. 4) | 900 | 65 | 18 | $3.2 \times 10^4$ | $6.2 \times 10^4$ |
| E (Ex. 5) | 800 | 60 | 40 | $2.2 \times 10^4$ | $5.1 \times 10^4$ |
| F (Ex. 6) | 480 | 50 | 80 | $3.4 \times 10^4$ | $6.5 \times 10^4$ |
| G (Ex. 7) | 570 | 60 | 100 | $5.0 \times 10^4$ | $3.0 \times 10^4$ |
| H (Ex. 8) | 450 | 60 | 100 | $7.5 \times 10^4$ | $3.7 \times 10^4$ |
| I (Ex. 9) | 700 | 65 | 20 | $5.0 \times 10^4$ | $4.8 \times 10^4$ |
| J (Ex. 10) | 720 | 65 | 20 | $5.0 \times 10^4$ | $4.5 \times 10^4$ |
| K (Ex. 11) | 700 | 65 | 20 | $5.2 \times 10^4$ | $4.8 \times 10^4$ |
| L (Ex. 12) | 600 | 55 | 25 | $3.1 \times 10^4$ | $3.0 \times 10^4$ |
| M (Ex. 13) | 900 | 65 | 15 | $2.8 \times 10^4$ | $2.5 \times 10^4$ |
| N (Ex. 14) | 900 | 65 | 15 | $2.7 \times 10^4$ | $2.4 \times 10^4$ |
| O (Ex. 15) | 800 | 65 | 20 | $1.8 \times 10^4$ | $2.0 \times 10^4$ |
| a (Comp. Ex. 1) | 450 | 45 | 150 | $0.9 \times 10^3$ | $2.7 \times 10^3$ |

What is claimed is:

1. A process for preparing a highly water-absorbent resin by a reversed-phase suspension polymerization method using an aqueous solution of a monomer containing an alkali metal salt of acrylic or methacrylic acid, water-soluble polymerization initiator, protective colloid, hydrophobic organic solvent and if required, dispersing agent, the process being characterized in that the protective colloid is a copolymer comprising:
   (A) about 50 to about 97 mole % of styrene and/or alkyl-substituted derivative thereof,
   (B) 0 to about 50 mole % of dialkylaminoalkyl acrylate or methacrylate and/or dialkylaminoalkyl acrylamide or methacrylamide,
   (C) about 3 to about 15 mole % of glycidyl acrylate and/or glycidyl methacrylate and
   (D) 0 to about 30 mole % of an unsaturated monomer which can be copolymerized with the component A, B or C.

2. A process as defined in claim 1 wherein the protective colloid is a copolymer comprising:
   (A) about 70 to about 95 mole % of styrene and/or alkyl-substituted derivative thereof,
   (B) about 3 to about 30 mole % of dialkylaminoalkyl acrylate or methacrylate and/or dialkylaminoalkyl acrylamide or methacrylamide, and
   (C) about 3 to about 15 mole % of glycidyl acrylate and/or glycidyl methacrylate.

3. A process as defined in claim 2 wherein the protective colloid is a copolymer comprising:
   (A) about 70 to about 95 mole % of styrene,
   (B) about 3 to about 30 mole % of diethylaminoethyl methacrylate, and
   (C) about 3 to about 15 mole % of glycidyl methacrylate.

4. A process as defined in claim 1 wherein the protective colloid is a copolymer prepared by suspension polymerization.

5. A process as defined in claim 1 wherein the protective colloid and the monomer containing an alkali metal salt of acrylic or methacrylic acid are used in a ratio by weight of the former to the latter of 0.5:99.5 to 30:70.

6. A process as defined in claim 5 wherein the protective colloid and the monomer containing an alkali metal salt of acrylic or methacrylic acid are used in a ratio of weight of the former to the latter of 0.7:99.3 to 10:90.

7. A process as defined in claim 1 wherein a dispersing agent is used.

8. A process as defined in claim 7 wherein the dispersing agent is selected from sorbitan fatty acid esters having HLB of about 2 to about 12 and saccharose fatty acid esters.

9. A process as defined in claim 8 wherein the dispersing agent is saccharose fatty acid ester.

10. A process as defined in claim 8 wherein the dispersing agent and the monomer containing an alkali metal salt of acrylic or methacrylic acid are used in a ratio by weight of the former to the latter of 0.001:100 to 10:100.

11. A process as defined in claim 1 wherein the aqueous solution of monomer containing an alkali metal salt of acrylic or methacrylic acid has a concentration of about 35 to about 80% by weight.

12. A process as defined in claim 11 wherein the aqueous solution of monomer containing an alkali metal salt of acrylic or methacrylic acid has a concentration of about 40 to about 70% by weight.

13. A process as defined in claim 1 wherein the hydrophobic organic solvent is at least one compound selected from the group consisting of cyclohexane, n-pentane and n-hexane.

14. A process as defined in claim 1 wherein the reversed-phase suspension polymerization is carried out at a temperature of about 40 to about 80° C.

15. A process as defined in claim 9 wherein the dispersing agent and the monomer containing an alkali metal salt of acrylic or methacrylic acid are used in a ratio by weight of the former to the latter of 0.001:100 to 10:100.

* * * * *